United States Patent [19]

Schoolman

[11] Patent Number: 4,559,555
[45] Date of Patent: Dec. 17, 1985

[54] STEREOSCOPIC REMOTE VIEWING SYSTEM

[76] Inventor: Arnold Schoolman, 8705 Catalina Dr., Prairie Village, Kans. 66207

[21] Appl. No.: 616,385

[22] Filed: Jun. 1, 1984

Related U.S. Application Data

[63] Continuation-in-part of Ser. No. 351,917, Feb. 24, 1982, abandoned.

[51] Int. Cl.$^4$ .................. H04N 13/00; H04N 7/18
[52] U.S. Cl. .................................. 358/88; 358/108; 358/210; 358/250
[58] Field of Search ................ 358/88, 92, 93, 108, 358/250, 210, 3; 350/174, 294

[56] References Cited

U.S. PATENT DOCUMENTS

| | | | |
|---|---|---|---|
| 2,995,156 | 10/1960 | Heilig | 358/88 |
| 3,049,588 | 8/1962 | Barnett | 358/88 |
| 3,504,122 | 3/1970 | Ratliff | 358/88 |
| 3,670,097 | 6/1972 | Jones | 358/91 |
| 3,833,300 | 9/1974 | Rymes | 358/250 |
| 3,883,689 | 5/1975 | Mansour | 358/227 |
| 3,919,475 | 11/1975 | Dukich | 358/210 |
| 3,923,370 | 12/1975 | Mostrum | 350/294 |
| 3,940,204 | 2/1976 | Withrington | 350/3.72 |
| 3,976,840 | 8/1976 | Cleveland | 364/900 |
| 4,028,725 | 6/1977 | Lewis | 358/103 |
| 4,034,401 | 7/1977 | Mann | 358/93 |
| 4,051,534 | 9/1977 | Dukich | 358/210 |
| 4,115,802 | 9/1978 | Kramer | 358/93 |
| 4,153,913 | 5/1979 | Swift | 358/93 |
| 4,160,263 | 7/1979 | Christy | 358/1 |
| 4,242,703 | 12/1980 | Tsuboshima | 358/150 |
| 4,246,607 | 1/1981 | Vijuerberg | 358/111 |
| 4,247,908 | 1/1981 | Lockhart | 364/900 |
| 4,266,271 | 5/1981 | Chamoff | 364/200 |
| 4,277,837 | 7/1981 | Stuckert | 364/900 |
| 4,298,176 | 11/1981 | Kendall | 358/88 |
| 4,310,849 | 1/1982 | Glass | 358/88 |
| 4,345,315 | 8/1982 | Cadotte | 364/900 |
| 4,347,508 | 8/1982 | Spooner | 358/250 |
| 4,360,875 | 11/1982 | Behnke | 364/900 |
| 4,395,731 | 7/1983 | Schoolman | 358/88 |
| 4,398,799 | 8/1983 | Swift | 350/174 |

OTHER PUBLICATIONS

*Aviation Week & Space Technology*, Oct. 11, 1982, pp. 133–134, "Technique Benefits Novice Technicians".

*Primary Examiner*—Howard W. Britton
*Attorney, Agent, or Firm*—Litman, Day and McMahon

[57] ABSTRACT

A stereoscopic remote viewing system includes a pair of spaced apart cameras mounted on a platform which is movable along a semicircular support track for azimuth aiming of the cameras. The track is pivotable about a diametric axis for elevation aiming of the cameras. The cameras are connected through selection switches to a head worn video display unit having a pair of cathode ray tubes (CRT's) mounted therein. Lenses and mirrors are positioned to project the images reproduced by the CRT's indirectly into the eyes of a viewer. A digital computer is connected through the selection switches and is employed for the storage and retrieval of texts and graphic information related to the operations viewed with the system.

14 Claims, 9 Drawing Figures

STEREOSCOPIC REMOTE VIEWING SYSTEM

CROSS-REFERENCE TO RELATED APPLICATION

This is a Continuation-in-Part application of U.S. patent application Ser. No. 351,917 for PORTABLE REMOTE TERMINAL WITH HEAD HELD DISPLAY filed Feb. 24, 1982, abandoned.

FIELD OF THE INVENTION

The present invention relates to remote video systems and, more particularly, to a stereoscopic video system with a head worn display for use as in the control of an industrial robot.

BACKGROUND OF THE INVENTION

Certain manufacturing operations lend themselves to performance by manually controlled industrial robots because of the hazardous nature of such operations. The hazards arise from the materials involved such as explosive, corrosive, pathogenic, cryogenic, radioactive or the like materials or from the necessity of performing such operations in atmospheres which are poisonous or non-life supporting to humans such as welding in inert gases or operations which require a vacuum. Other situations which benefit from manually controlled robotics include operations which are necessarily carried out by remote control such as some deep sea operations and outer space operations. While some such operations can be performed by automatically controlled robots with feedback loops for self-correction, others require direct human control.

The primary human feedback senses for manual activities are usually vision and touch or feel. Considerable effort has been expended in the development of remote controls which have a useful feel such that a given amount of manual movement of a control results in an expected result. A portion of the success of such a control involves learning to use the control by the operator.

The development of "remote sight" has, to an extent, lagged the development of remote manipulation because of the complexities of human vision and the complexities of the systems for aiding human vision, namely, television. Human vision is stereoscopic; that is, the right and left eyes sense slightly different images because of the lateral separation therebetween. The brain interprets the difference in image to derive depth perception such that a three dimensional visual sense results. Through practice as an individual ages, eye-hand coordination can become quite accurate.

Television has for the most part been a two dimensional medium, notwithstanding such techniques in color television as so-called "3D" effects wherein two of the component colors, such as red and green, are offset laterally and when viewed through a set of properly oriented red and green spectacle lenses gives an approximation of three dimensional vision. Such effects, while arguably adequate for applications as in motion pictures, do not convey an accurate enough sense of depth for such activities as the control of a robotic arm. In order to obtain a truer video image of the depth dimension, that is in the direction of the line of sight of a video camera, a second video camera which is laterally spaced or elevated from the first camera has been required. A viewer is then required to watch and coordinate the images on two separate viewing screens. The result is an improvement over two dimensional viewing, but does not provide the apparent simplicity and the convenience of natural vision.

In more recent years, image (video camera) tubes and picture tubes, or cathode ray tubes (CRT's), have been miniaturized to the extent that a pair of image tubes can be positioned to approximate the perspective of the human eyes; and a pair of CRT's can be positioned and the images projected preferably indirectly, to the eyes of a human such that a good approximation of natural stereoscopic vision can be achieved. Non-CRT visual display devices such a liquid crystal, light emitting diode, and fluorescent matrix displays are currently being applied to reduce the size of video displays even further.

SUMMARY OF THE INVENTION

The present invention provides apparatus for stereoscopically viewing a remote subject. The apparatus includes a pair of video cameras mounted on a platform which is capable of movement in three dimensions. The cameras include motors for focus and zoom control and convergence motors such that the lines of sight of the cameras coincide at the focal point of the cameras. The camera platform is mounted on a semicircular track and is movable therealong for azimuth aiming of the cameras. The track is rotatable about a diametric axis for elevation of the cameras.

The cameras are coupled to a head worn video display unit including means such as a helmet with a pair of video display devices such as miniature cathode ray tubes or picture tubes and optical and mirror or prismatic elements to project the displayed images into focus in the eyes of a viewer wearing the video display. The helmet also includes circuitry for generating sweep signals for the CRT's and circuits for processing the video signals from the cameras.

A computer system is connected to the stereoscopic display through a video source selector for the display of reference texts and graphics related to the operation to be performed by a robotic device associated with the viewing system. For displaying texts and graphics which do not require a stereoscopic display, the computer is controlled to feed the same image to the right and left video channels for a binocular monoscopic view of such information.

OBJECTS OF THE INVENTION

The principal objects of the present invention are: to provide an improved apparatus for remotely viewing manually controlled operations; to provide such an apparatus which facilitates the remote operation of a robotic arm and hand device; to provide such an apparatus which provides a three dimensional or stereoscopic view of a remote operation; to provide such an apparatus including a pair of movably mounted video cameras and a corresponding pair of video displays adapted as a head worn stereoscopic unit for placement on the head of a viewer to project a pair of images from the cameras into the eyes of the viewer; to provide such an apparatus wherein the cameras are mounted on a bracket or platform which is positioned on a semicircular track for movement along the track for azimuth aiming of the cameras, the semicircular track being rotatable about a horizontal diametric axis for elevation aiming of the cameras; to provide such an apparatus including controls for focusing the cameras and zooming of the cameras to change perspective and viewed size of the subject; to provide such an apparatus including means for maintaining the focus and line of sight convergence of the cameras during zooming; to provide such an apparatus including a computer selectively connected to the stereoscopic display unit for the display of texts and graphic information related to the operation performed during use of the viewing system; and to provide such a stereoscopic viewing system which is economical to manufacture, convenient in operation, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE PREFERRED EMBODIMENTS

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a stereoscopic remote viewing system according to the present invention. The system 1 generally includes a pair of video cameras 2 and 3 mounted on a three dimensionally movable camera aiming support 4 and a pair of video display devices 5 and 6 (FIGS. 5–7) mounted in a video display unit 7 which is adapted to be worn on the head of a viewing individual. The display unit 7 includes video circuitry 8 (FIG. 8) to adapt the display devices 5 and 6 as video monitors for viewing the images sensed by the cameras 2 and 3. The cameras 2 and 3 are positioned to capture a stereoscopic view of a scene; and similarly the display devices 5 and 6 are positioned to provide a stereoscopic display of the reproduced images for the viewer. A system control console 9 allows the viewer to control the position and the optical features of the camera 2 and 3. A computer system 10 is selectively connected to the video display unit 7 and is employed to store and retrieve digitally encoded texts and graphics for display on the video display unit 7. The system 1 is particularly adapted for remotely viewing operations such as the operations of a remotely controlled robotic device 10.

Figures 3, 4:
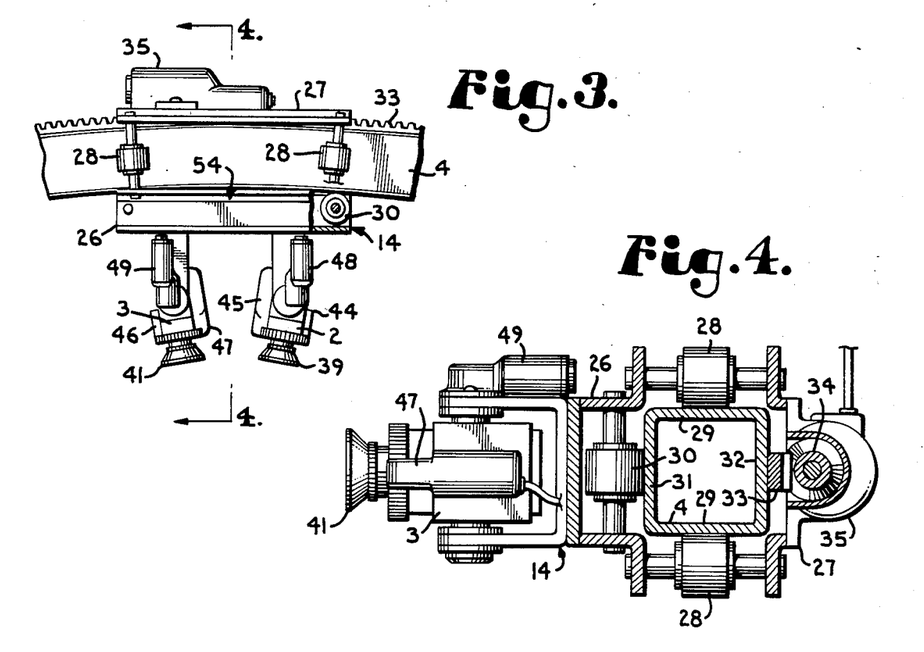
FIG. 3 is an enlarged fragmentary plan view of the video camera platform.
FIG. 4 is a further enlarged sectional view taken on line 4—4 of FIG. 3 and illustrates details of the video camera unit.

Referring to FIG. 3, the cameras 2 and 3 are mounted in spaced relation on a camera bracket or platform 14 which is, in turn, mounted for movement along the camera aiming support 4. The support 4 is a semicircular guide track which is pivotally connected at extremities of the track 4 to track supports 15 for rotation of the track 4 about a horizontal diametric axis 16 of the track 4. The illustrated track 4 has square tubular cross section. The extremities 17 of the track 4 extend past the pivot joints 18 which connect the track 4 to the supports 15. The extremities 17 preferably have counterweights 19 thereon to counterbalance the track structure on the pivot joints 18. An elevation motor 20 is mounted on one of the track supports 15 and operatively engages the track 4 to pivot same for elevation aiming of the cameras 2 and 3. For example, a helical or worm gear in a housing 21 is positioned on a rotary shaft of the motor 20 and engages a pinion gear in a housing 22 and fixed on a pivot shaft 23 of the track 4. The degree of angular movement of the track 4 which is allowable or desired is determined by the dimensions of the track 4 in comparison to the height of the supports 15 and the degree of coverage of the operation required. Preferably, the track 4 is able to cover at least a hemisphere.

The camera platform 14 may be any structure which supports the cameras 2 and 3 for movement along the track 4. The platform 14 illustrated in FIG. 4 includes an inner bracket 26 and an outer bracket 27 joined by sets of opposed side rollers 28 which contact side walls 29 of the track 4. An inner set of rollers 30 engages an inside wall 31 of the track 4. The outer wall 32 has an elongated rack gear 33 positioned on the outer surface thereof. The gear 33 cooperates with a helical or worm gear 34 which is affixed to the rotary shaft of an azimuth motor 35 which is mounted on the outer bracket 27. Rotation of the worm gear 34 causes the platform 14 to move along the track 4 for azimuth aiming of the cameras 2 and 3. The rollers 28 and 30 are preferably resiliently urged against the respective walls of the track 4 such that the platform 14 is securely held on the track 4.

Figure 9:
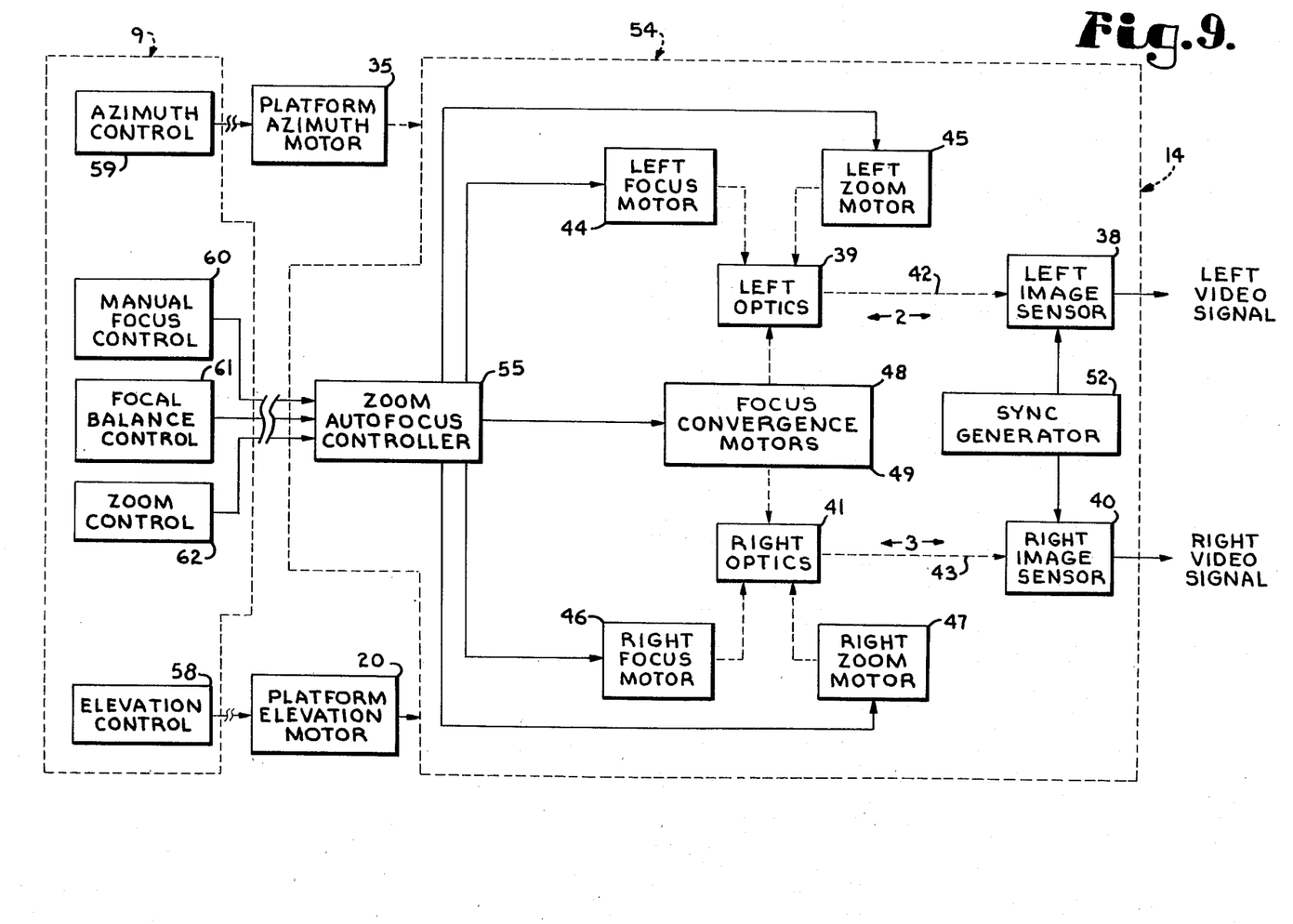
FIG. 9 is a block diagram illustrating controls for operation of the camera unit of the viewing system.

Referring to FIGS. 3, 4, and 9, the left hand camera 2 includes a left image sensor 38 and left camera optics 39 while the right camera 3 includes a right image sensor 40 and right camera optics 41. The image sensors 38 and 40 may be any type of conventional video image sensors including solid state image sensors. The optics 39 and 41 are mounted in the cameras 2 and 3 for movement along respective lines of sight or optical axes 42 or 43 to focus an image on the associated image sensor and to change the optical perspective of the image transmitted to the associated image sensor. For these purposes, the left video camera 2 includes a left focus motor 44 and a left zoom motor 45 while the right video camera 3 includes a right focus motor 46 and a right zoom motor 47. In order for a useful stereoscopic image to be sensed by the pair of cameras 2 and 3, it is necessary for the cameras to be aimed such that the scenes sensed by the cameras 2 and 3 substantially overlap, that is, such that the focal points of the cameras 2 and 3 substantially coincide. Therefore, the cameras 2 and 3 include focus convergence motors 48 and 49 respectively. The cameras 2 and 3 are mounted for rotation substantially in the plane of the platform track 4 and have the motors 48 and 49 connecting the associated cameras to the inner bracket 26 of the camera platform 14. The focus convergence motors 48 and 49 are activated to maintain the coincidence of the focal points of the cameras 2 and 3 as the focal points of the cameras are changed by operation of the focus motors 44 and 46.

In order to prevent undesired visual effects between the left and right video channels, the left and right image sensors 38 and 40 are provided with common sync signals provided by a sync generator 52 such that the scans of the left and right image sensors 38 and 40 are synchronized. Preferably, the cameras 2 and 3 include means for maintaining focused images as the optics 39 and 41 are zoomed. Mechanical arrangements for maintaining focus during zooming are known and may be employed in the system 1. As illustrated in FIG. 9, the camera unit 54 includes a zoom autofocus controller 55 which is a dedicated control computer interconnected with the focus motors 44 and 46, the zoom motors 45 and 47, and the focus convergence motors 48 and 49. Autofocus controller arrangements for monoscopic lens systems are known. The autofocus controller 55 is adapted for maintaining the focus during zooming for the left and right cameras 2 and 3 and, further, controls the convergence of the focal points of the cameras 2 and 3. Although not detailed in FIG. 9, sensors would be required for determining the positions of the left and right optics 39 and 41 for the generation of autofocus control signals. Such sensing could include shaft encoders of various descriptions positioned on the shafts of the motors of the camera unit 54. The details of such position sensors are believed to be within the capabilities of one skilled in the digital control of electric motors.

The viewing system control panel 9 includes an elevation control 58 connected to the platform elevation motor 20 and an azimuth control 59 connected to the platform azimuth motor 35. The manual focus control 60 is provided for fine adjustment of the focal positions of the left and right optics 39 and 41 in unison. A focal balance control 61 provides for differential adjustment of the focal positions of the optics 39 and 41 to compensate for the individual visual acuities of the user of the system 1. A zoom control 62 is operated to cause zooming of the left and right optics 39 and 41 in unison. The controls 60, 61, and 62 are operatively connected to the motors of the camera unit 54 through the zoom autofocus controller block 55.

Figures 5, 6:
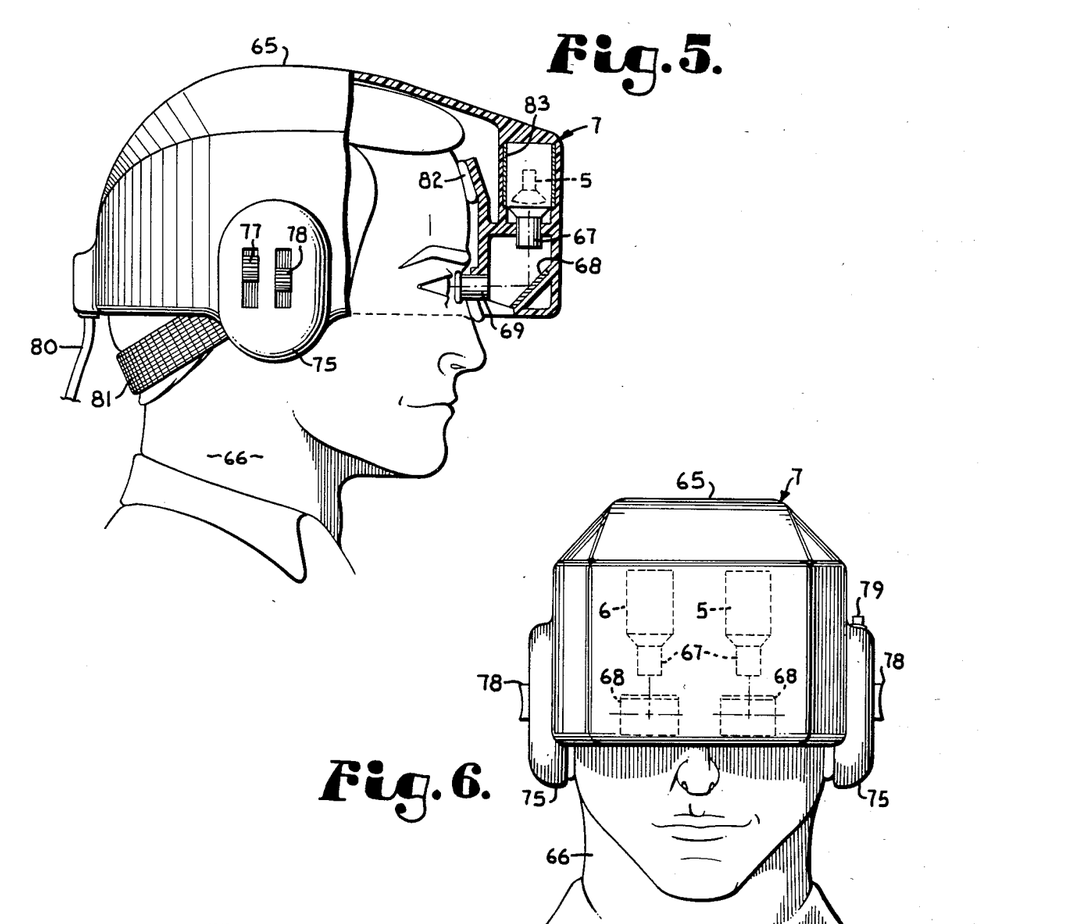
FIG. 5 is a side elevational view of a stereoscopic display unit of the system with portions broken away to illustrate the optical elements which project a pair of images into the eyes of the viewer.
FIG. 6 is a front elevational view of the display unit of the system.
Figure 7:
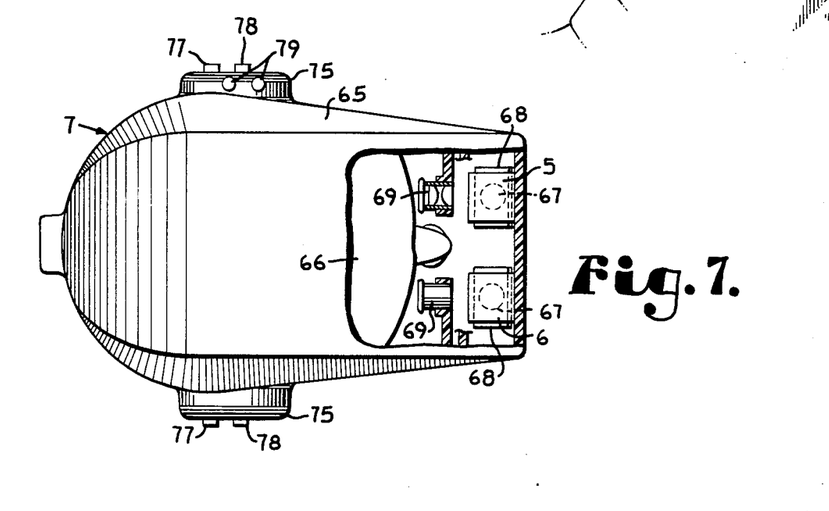
FIG. 7 is a top plan view of the display unit with portions broken away to illustrate further details of the projection optics.

FIGS. 5-7 illustrate details of the head worn video display unit 7. The unit 7 includes a cap or helmet 65 in which the components of the unit 7 are mounted. The illustrated video display devices 5 and 6 are CRT's and are mounted within the helmet 65 for indirect projection of the images therefrom into the eyes of the viewer 66 in order to decrease the possibility of projecting X-rays into the eyes of the viewer. The use of solid state matrix displays instead of the CRT's 5 and 6 is contemplated such that the system 1 is not to be limited to the use of CRT's as video display devices. The CRT's 5 and 6 are mounted for downward projection of the images thereof through projection optical elements 67 toward right angle reflecting elements 68 such as mirrors or prisms and from there through viewing lenses 69 to the eyes of the viewer 66. The viewing lenses 69 are provided to compensate for the short focal distance between the eyes of the viewer 66 and the display devices 5 and 6 such that the images can be focused at a greater effective distance. The viewing lenses 69 are preferably finely adjustable to accommodate the visual capabilities of the eyes of the viewer 66. Further, the lateral positions of the right and left video display components are preferably adustable to accommodate the spacing between the eyes of the viewer 66, although such adjustment means are not illustrated.

Figure 8:
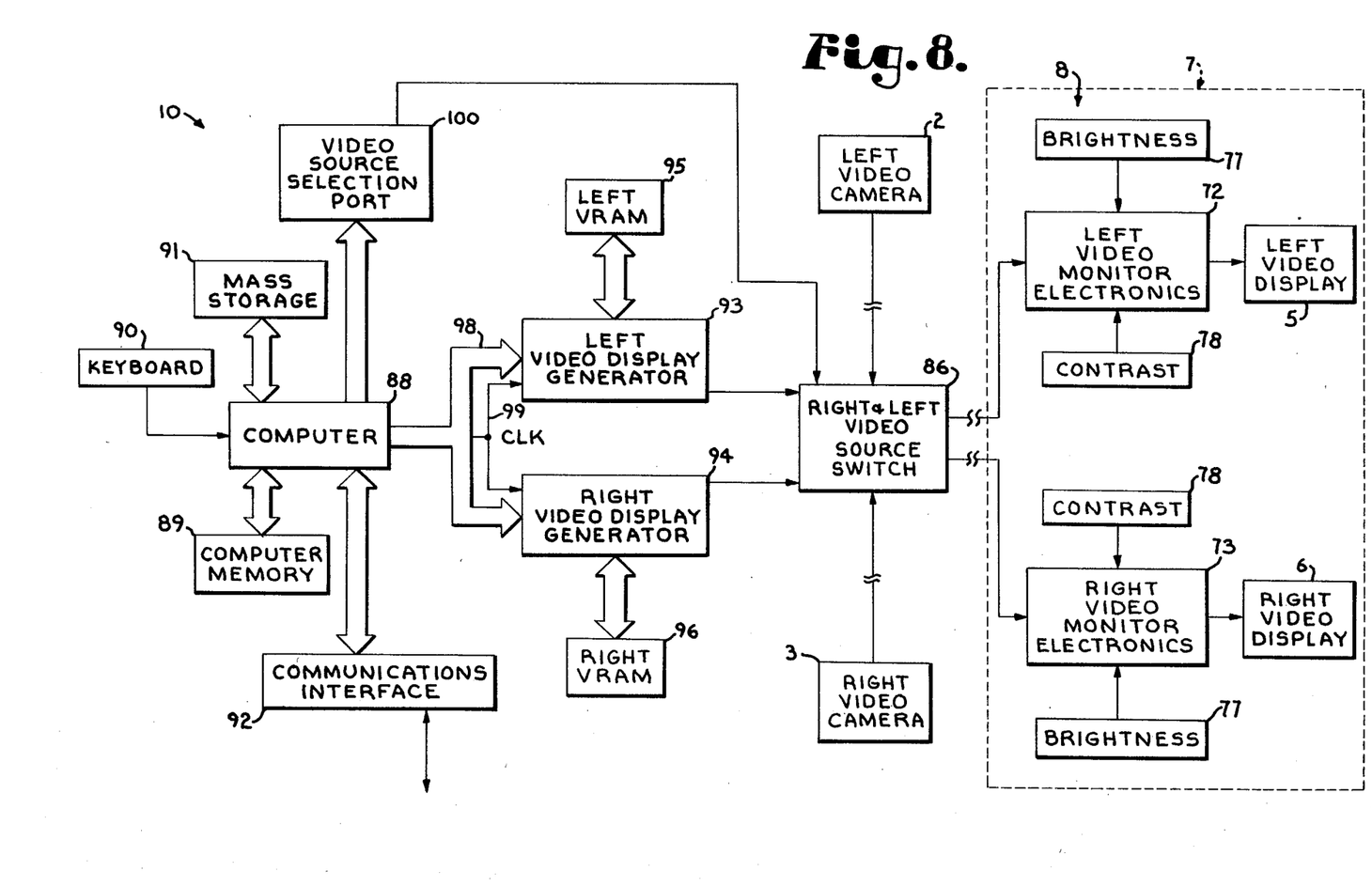
FIG. 8 is a block diagram illustrating the functional relationships of a computer system for storing and recalling texts and graphics related to the operation performed and viewed through the viewing system, a pair of video cameras, and the display unit.

Currently, color cathode ray tubes are not small enough for convenient use in the video display unit of the system 1. Therefore, using CRT's, the system 1 is restricted to monochrome or black and white technology. However, color liquid crystal matrix displays are known such that in general, the system 1 is not intended to be restricted to black and white viewing. With reference to FIG. 8, the components of the video display unit 7 comprise a head worn stereoscopic video monitor unit. Therefore, the left and right video channels include respective left and right video monitor circuitry 72 and 73. The monitor circuits 72 and 73 include sweep generators for generating the rasters on the displays 5 and 6 and further include video signal demultiplexers for separating sync and luminance signals from composite signals if such composite signals are employed, and conventional video circuits for processing and displaying the images represented by the video signals. If color technology is employed in the system 1, it is foreseen that the color component signals may either be provided as right and left color composite signals or as separated red, green, and blue (RGB) sets of color signals. The left and right monitor circuits are conventional and are configured according to the requirements of the system. It is preferred that the circuits 72 and 73 be mounted within the helmet 65 such as within ear bosses 75 or in an enlargement such as at the rear of the helmet 65 (not shown) to provide better balance of the helmet 65. Preferably, each of the circuits 72 and 73 includes at least a brightness control 77 and a contrast control 78 for adjustment of the displayed images. If color is provided in the system 1, color level and tint or individual RGB color controls (not shown) would appropriately be provided. In addition, an on/off-power switch 79 is provided for activating and deactivating the components within the video display unit 7.

The video signals from the cameras 2 and 3 are provided to the components within the helmet 65 as by a cable 80 which conveniently enters the video display unit 7 at the rear of the helmet 65. Although not illustrated, the helmet 65 preferably includes an adjustable harness for fitting the helmet to the head of the viewer 66. Means such as an elastic band 81 may be provided to retain the helmet in position on the head of the viewer. A forehead pad 82 is provided to maintain the position of the optical elements of the display unit 7 in relation to the eyes of the viewer. X-Ray shields 83 are preferably positioned to enclose the CRT's 5 and 6, particularly if color CRT's are employed.

The video signals from the left and right video cameras 2 and 3 are provided to the video display unit 7 through a right and left video source switch 86. The video source switch 86 also has the video output from the computer system 10 connected thereto whereby the video display unit 7 may be driven either by the computer system 10 or the video cameras 2 and 3. The video source switch 86 may include conventional switch components or coaxial switch components which are properly sequenced to isolate one video source from another. Preferably, the video source switch components are operated by solenoid means (not shown) under control of the computer system 10. The switch 86 may be further expanded to provide for selection of other video sources such as video tape recorders, video discs, or television tuners (not shown). Further, it is foreseen that the video source switch 86 could be configured to allow the routing of video signals from the cameras 2 and 3 to the video display unit 7 and, additionally, to video recording devices to record the images as viewed for later analysis or for digitization and storage within a computer system such as the computer system 10.

The computer system 10 is, for the most part, a conventional general purpose digital computer. The illustrated computer system 10 includes a central processing unit or main computer board 88, a main computer memory 89, a keyboard 90, mass storage devices such as discs 91, and a communications interface 92 for communication between the computer system 10 and another computer. Normally, computers, particularly microcomputers, only require a single video channel for displaying text or graphics on a video monitor associated therewith. However, since the capability for stereoscopically displaying digitized graphic information is desired, the computer system 10 has left and right video channels interfaced thereto. The left and right hand video channels include respectively a left and a right video display generator 93 and 94. The video display generators 93 and 94 include associated video memories or video random access read/write memories (VRAM) 95 and 96. In general, the video display generators derive respective analog video signals from the digital information stored within the video memories 95 and 96. Further, the generators 93 and 94 control the flow of digital data from the computer 88 to the video memories 95 and 96. The video display generators 93 and 94 are essentially conventional and are preferably capable of high resolution displays. The generators 93 and 94 include respective address decoders for the proper routing of video information from the computer board 88 to the generators 93 and 94 over a video bus 98 which is interfaced to the computer board 88 through a video port. In order to synchronize the left and right video displays 5 and 6 when the computer video channels are selected, the right and left video display generators 93 and 94 are connected to a common clock line 99 of the video bus 98. The video source switch 86 receives a selection command from a video source selection port 100 which is interfaced to the computer board 88. The operator or viewer 66 selects the desired video source by operation of a key or keys on the keyboard 90.

The computer system 10 includes software for operation of the video source switch 86 and for storing, retrieving, and routing digitized images from the mass storage device 91 to the video display unit 7. The digitized images provided by the computer system 10 may be either stereoscopic or monoscopic whereas text which is displayed on the unit 7 need only be monoscopic. For monoscopic displays, the computer 88 feeds the same display data to the left and right display generators 93 and 94. For stereoscopic displays, different video data is routed to the left and right display generators 93 and 94. The computer system 10 may be programmed to display a menu upon the operation of a selected key on the keyboard 90 for the selection of functions related to the system 1 or may be programmed to respond to specific spelled-out commands.

Figure 1:
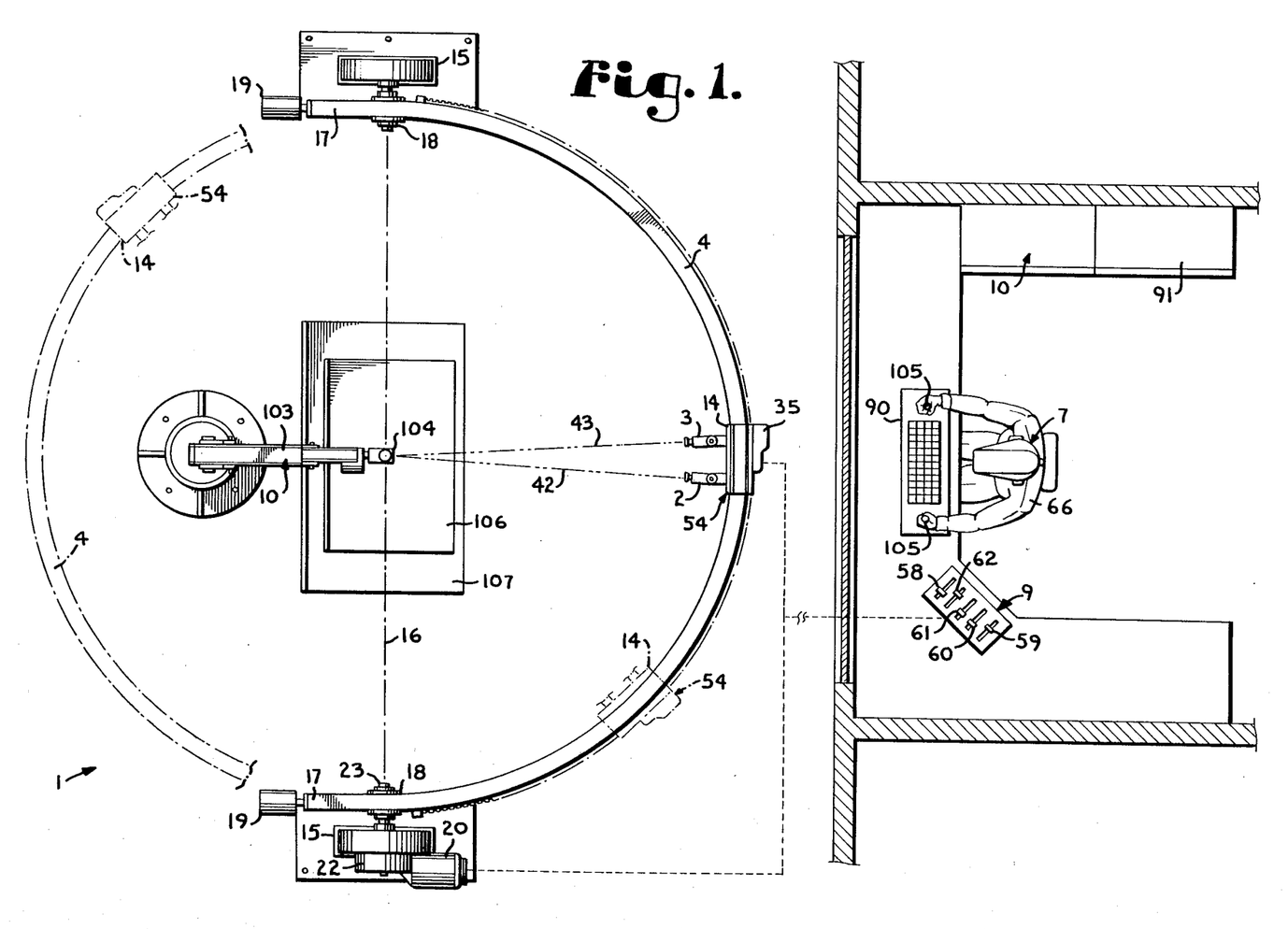
FIG. 1 is a diagrammatic plan view of a stereoscopic remote viewing system according to the present invention, shown in association with a manually controlled robotic device.
Figure 2:
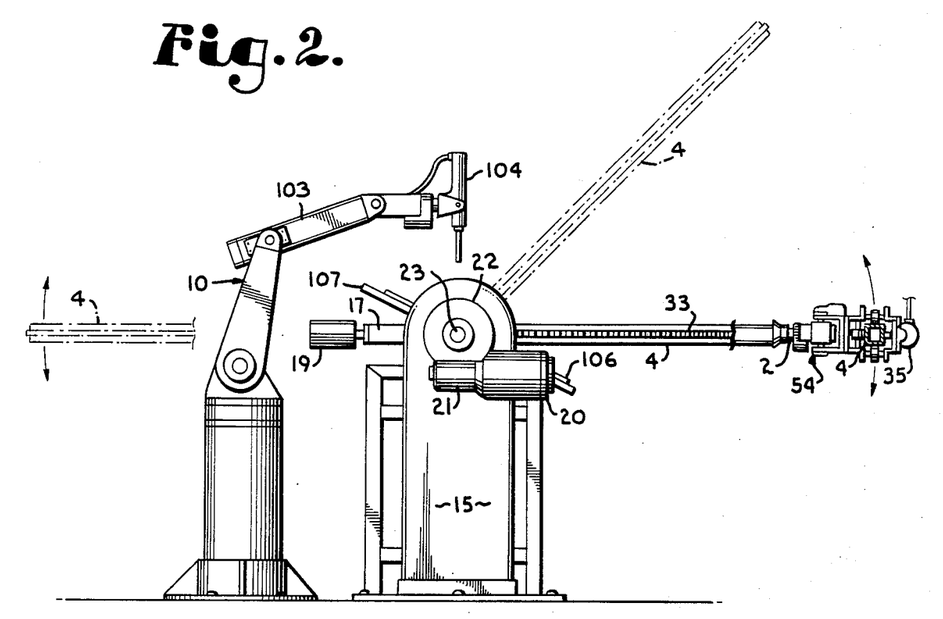
FIG. 2 is a side elevational view of a movable camera platform support of the system.

The viewing system 1 is particularly well adapted for remotely viewing an operation such as detailed manufacturing operations performed by a manually controlled robotic device. The robotic device 10 illustrated in FIGS. 1 and 2 includes a robotic arm 103 having a tool 104 attached thereto. The robotic device 10 is controlled as by the manipulation of robot control levers 105 which may be associated with either the control console 9 or the keyboard 90. The robotic arm 103 is controlled to selectively position the tool 104 for operations on a workpiece 106 positioned on a workpiece support 107. During the operation, the camera unit 54 may be placed anywhere along the platform guide track 4 and the track pivoted about its axis 16 to provide the best view to the operator 66. The stereoscopic images provided by the system 1 greatly facilitates the remote placement of the tool 104 in three dimensional space with respect to the workpiece 106. The computer system 10 provides for the display of texts such as instructions or procedures related to the operations performed by the robotic device 10 and viewed by the viewing system 1. Further, diagrammatic information and three dimensional graphic information can be recalled by the computer system 10 from the mass storage device 91 and displayed on the video display unit 7 for viewing by the operator 66. Such graphic information is intended to relate to the operations performed with the robotic device 10 and may include patterns for comparison with the workpiece being operated upon, views of a finished product, and the like.

It is to be understood that while certain forms of the present invention have been illustrated and described herein, it is not to be limited to the specific forms or arrangement of parts described and shown.

What is claimed and desired to be secured by Letters Patent is as follows:

1. A stereoscopic remote viewing system comprising:
   (a) a pair of spaced apart image sensor means providing a left video signal and a right video signal, said video signals representing scenes as sensed by said image sensor means;
   (b) camera platform means having said image sensor means mounted thereon for convergence of lines of sight of said sensor means substantially at a subject to be viewed;
   (c) camera platform aiming means supporting said platform means for movement in three dimensions to selectively aim said image sensor means;
   (d) platform aiming motor means connected with said aiming means to move said aiming means;
   (e) aiming control motor means connected to said motor means for manipulation by a viewer using said viewing system to aim said camera platform means;
   (f) a pair of video display devices operatively connected respectively to said image sensor means to receive said left and right video signals and displaying images which are reproductions of scenes sensed by said image sensor means; and (g) head unit means supporting said video display devices for viewing the images reproduced by said display devices, said head unit means being adapted for wearing on the head by said viewer.

2. A system as set forth in claim 1 including:
(a) computer means for the storage and retrieval of text and graphic information; and
(b) video source selector means for selectively connecting said video display devices to said computer means and said image sensor means.

3. A system as set forth in claim 1 wherein:
(a) said video display devices are cathode ray tubes (CRT's); and
(b) said head unit means includes optical elements positioned to project images reproduced on said CRT's indirectly into the eyes of said viewer.

4. A system as set forth in claim 1 wherein each image sensor means includes:
(a) an image sensor device;
(b) optic means positioned in relation to said image sensor device to define a line of sight of said image sensor device; and
(c) a focus motor connected to said optic means for positioning said optic means to focus a scene at a focal point along said line of sight on said image sensor device.

5. A system as set forth in claim 4 wherein each image sensor means includes:
(a) a zoom motor connected to said optic means to vary the optical perspective of said scene as focused on said image sensor device.

6. A system as set forth in claim 5 including:
(a) convergence motor means connected between said image sensor means and said camera platform means for movement of said image sensor means to intersect the lines of sight of said image sensor means for substantial coincidence of the focal points of said image sensor means.

7. A system as set forth in claim 5 including:
(a) autofocus means connected to the focus motors and the zoom motors to maintain the focus of said image sensor means during the operation of said zoom motors.

8. A system as set forth in claim 4 including:
(a) focal balance control means operatively connected to the focus motors for the fine adjustment of the focus positions of said optic means to compensate for the individual visual acuities of the eyes of said viewer.

9. A system as set forth in claim 1 wherein said camera platform aiming means includes:
(a) a substantially semicircular platform track;
(b) platform track support means supporting said platform track for elevation pivoting about a horizontal diametric axis of said track; and
(c) said camera platform means being supported on said track for movement therealong.

10. A system as set forth in claim 9 wherein said platform aiming motor means includes:
(a) an azimuth motor engaged between said platform means and said track for movement of said platform means along said track to motivate the azimuth aiming of said platform; and
(b) an elevation motor engaged between said track and said track support means to pivot said track about said diametric axis to motivate the elevation aiming of said platform means.

11. A system as set forth in claim 10 including:
(a) a rack gear extending along said platform track;
(b) said azimuth motor being mounted on said camera track support means and having a rotary shaft; and
(c) a helical gear positioned on said shaft and engaging said rack gear whereby rotation of said shaft urges said platform means along said platform track.

12. A system as set forth in claim 10 including:
(a) a pinion gear affixed to said platform track, said gear having a gear axis positioned coaxially with said diametric axis of said track;
(b) said elevation motor being mounted on said platform means and having a rotary shaft; and
(c) a helical gear positioned on said shaft and engaging said pinion gear whereby rotation of said shaft causes the pivoting of said platform track about said diametric axis.

13. A system as set forth in claim 1 in combination with:
(a) robotic tool means manually controlled by a wearer of said head unit means for viewing the operations performed by said tool means with said viewing system.

14. A stereoscopic remote viewing system comprising:
(a) a pair of spaced apart image sensor means providing a left video signal and a right video signal, said video signals representing scenes as sensed by said image sensor means;
(b) camera platform means having said image sensor means mounted thereon for convergence of lines of sight of said sensor means substantially at a subject to be viewed;
(c) a substantially semicircular platform track;
(d) platform track support means supporting said platform track for elevation pivoting about a horizontal diametric axis of said track;
(e) said camera platform means being supported on said track for movement therealong;
(f) an azimuth motor engaged between said platform means and said track for movement of said platform means along said track to motivate the azimuth aiming of said platform;
(g) an elevation motor engaged between said track and said track support means to pivot said track about said diametric axis to motivate the elevation aiming of said platform means;
(h) camera aiming control means connected to said azimuth and elevation motors for manipulation by a viewer using said viewing system to aim said camera platform means;
(i) a pair of cathode ray tubes (CRT's) operatively connected respectively to said image sensor means to receive said left and right video signals and displaying images which are reproductions of scenes sensed by said image sensor means;
(j) head unit means supporting said CRT's for viewing the images reproduced thereby, said head unit means being adapted for wearing on the head by said viewer;
(k) said head unit means including optical elements positioned to project images reproduced on said CRT's indirectly into the eyes of said viewer;
(l) computer means for the storage and retrieval of text and graphic information; and
(m) video source selector means for selectively connecting said CRT's to said computer means to display said text and graphic information and said image sensor means to display images of scenes sensed by said image sensor means.

* * * * *